United States Patent [19]

Kunzler et al.

[11] Patent Number: 4,833,262

[45] Date of Patent: May 23, 1989

[54] OXYGEN PERMEABLE POLYMERIC MATERIALS

[75] Inventors: Jay F. Kunzler, Canandaigua, N.Y.; Virgil Percec, Pepper Pike, Ohio

[73] Assignee: Bausch & Lomb Incorporated, Rochester, N.Y.

[21] Appl. No.: 84,538

[22] Filed: Aug. 12, 1987

[51] Int. Cl.$^4$ ............................................. C07F 7/08
[52] U.S. Cl. ..................................................... 556/488
[58] Field of Search ......................................... 556/488

[56] References Cited

U.S. PATENT DOCUMENTS

| | | | |
|---|---|---|---|
| 2,671,795 | 9/1954 | Frisch et al. | 556/488 X |
| 3,249,630 | 5/1966 | Viehe | 556/488 X |
| 4,307,241 | 12/1981 | Trost et al. | 556/488 X |
| 4,458,087 | 7/1984 | McAlister | 556/488 X |
| 4,567,245 | 1/1986 | Takamizawa et al. | 526/279 |

OTHER PUBLICATIONS

J. Am. Chem. Soc., 1983, 105, 7473.

Primary Examiner—Paul F. Shaver
Attorney, Agent, or Firm—Bernard D. Bogdon; Christopher E. Blank

[57] ABSTRACT

A polymer represented by the general formula

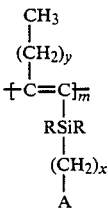

where m is the average degree of polymerization of the polymer, y is an integer from 1 to 3, x is an integer from 1 to 10, A denotes a halogen atom and R denotes an alkyl radical with 1 to 6 carbon atoms.

2 Claims, No Drawings

OXYGEN PERMEABLE POLYMERIC MATERIALS

BACKGROUND OF INVENTION

Contact lenses can be divided into two general types, hard contact lenses and soft contact lenses. Hard contact lenses are generally made of polymethylmethacrylate plastic and copolymers thereof. Soft contact lenses are made from a wide variety of plastics. The most common type of soft contact lens materials are referred to as hydrogels the most basic of which is poly(2-hydroxy)ethylmethacrylate). Numerous variations of this type of material have been developed to enhance various physical characteristics important in contact lenses such as wettability, water content, stability and physical strength. Other soft lens materials include n-vinyl lactam or vinyl pyrrolidone-based polymers and siloxane-based polymers.

Polysiloxane-based polymers possess many interesting characteristics. They are highly oxygen permeable, and they are relatively inert. However, polysiloxanes have a number of shortcomings. The lenses must be molded, they are susceptible to protein deposition, and they are not easily "wetted". Various formulations have been proposed in order to solve the various problems associated with polysiloxane where used in contact lenses.

Recently polyacetylenes have been proposed as being highly oxygen permeable. For instance, U.S. Pat. No. 4,567,245 issued to Takimizawa, et al. teaches that a copolymer of

and

is a highly oxygen-permeable polymer particularly suited because of its high oxygen permeability to use in contact lenses. Poly((1-trimethylsilyl)-1-propyne) is also known as a highly oxygen-permeable material. J. Am. Chem. Soc. 1983, 105, 7473. The present invention provides a novel class of polyacetylenes which can be tailored with respect to their surface properties and with respect to their other physical properties to provide materials useful in the construction of contact lenses.

SUMMARY OF THE INVENTION

This invention relates to a class of novel acetylene functional compounds which are useful as monomers used to form novel, highly oxygen permeable polymers. The invention also relates to these novel, highly oxygen permeable polymers. In general the novel acetylene functional compounds are represented by the general formula

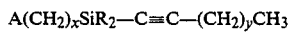

where A denotes a halogen atom, preferably a bromine atom; R denotes an alkyl radical with 1 to 6 carbon atoms; x is an integer from 1 to 10, preferably 3 to 6; and y is an integer from 0 to 3. The invention relates to polymers and copolymers of such acetylene functional monomers, and functionally modified products of such polymers.

DETAILED DESCRIPTION

The present invention relates to a novel class of compounds which are useful monomers in the synthesis of polyacetylene polymers. These novel monomers are represented by the general formula

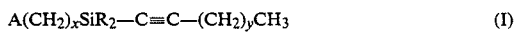

where A denotes a halogen atom, R denotes an alkyl radical with 1 to 6 carbon atoms, x is an integer from 1 to 10, preferably from 3 to 6, and y is an integer from 0 to 3.

Specifically, these monomers include 1-(4-bromobutyldimethylsilyl)-1-propyne, 1-(4-bromobutyldiethyl)-1-propyne, and 1-(4-bromobutyldimethyl)-1-butyne. These monomers can be synthesized by reacting a haloalkyldialkylchlorosilane of the general formula

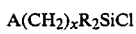

where A, R and x are as defined above, with an alkyllithium compound.

The present invention also relates to the polyacetylene polymers produced by polymerizing the monomers of general formula (I). These polyacetylene polymers can be represented by the general formula

where m denotes the average degree of polymerization of the polymer, and A, R, x and y are defined as above.

The monomers can also be reacted with the monomer 1-trimethylsilyl-1-propyne to form a copolymer which can be represented by the general formula

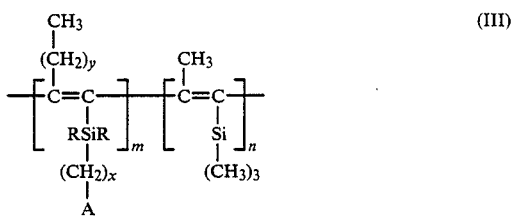

where A, R, x, and y are as defined above, m+n represents the average degree of polymerization of the polymer and n/m+n and m/m+n represent the mole percent of each respective monomer in the polymer.

Synthesis of the polymers and copolymers of the invention can be accomplished by adding the monomer, or a mixture of the monomer with 1-trimethylsilyl-1-propyne, to a chlorobenzene solution of tantalum pentachloride, niobiumpentachloride, or the like. The final, purified product can be obtained by precipitating the reaction mixture with a nonsolvent of the polymeric product such as methanol.

The resultant polymers of formula (III) can be further reacted with various agents to form functionalized polyacetylene. These functionalized polymers are synthesized by substituting an organofunctional moiety for the halo moiety. The particular synthetic steps depend upon the particular organofunctional moiety used. The types of moieties which can be used include methacrylate, styrene, quaternary ammonium salts, acetate, and alcohol functional moieties. These functionalized polymers can be represented by the general formula (II) and (III) given above where A denotes one of the organofunctional moieties.

By functionalizing the polyacetylene polymers one can achieve a number of desirable characteristics in the new polymer. One can improve the surface properties of the polymer, provide increased crosslinking capacity, and tailor the surface properties of the resulting polymer.

All of the polymers within the scope of the present invention exhibit high oxygen permeabilities which make them particularly useful materials for prosthetic devices, particularly devices that require such high permeabilities. The materials are particularly useful in contact lenses.

The molecular weights of the polymers, both the halo moiety containing polymers and the functionalized polymers can be controlled by varying the mole ratio of initiator to monomer used in the synthesis. The molecular weight of the polyacetylene polymer is directly related to this ratio in an almost linear fashion. The mechanism of the polymerization is believed to be similar to the metathesis polymerization of olefins, i.e. propagation proceeds through metal carbenes and metal cyclobutenes. Due to steric hindrance, it is believed the polymerization minimizes backbiting of the polymer, and hence the polymerization is a living polymerization. Addition of extra monomer to the polymer results in further polymerization.

EXAMPLES

Synthesis of Monomers

Synthesis of 1-trimethylsilyl-1-propyne 0.4 mole of trimethylchlorosilane was slowly added to 300 ml of an ice-water cooled, dry ether suspension of 0.5 mole propynllithium. The mixture was refluxed for four hours, cooled to 5° C., and washed three times with distilled H$_2$O. The ether layer was collected and dried over MgSO$_4$. The product was fractionally distilled and had a boiling point of 98°–100° C. at 760 mm Hg pressure. Yield was 90.1% of theoretical. H' NMR confirmed the structure. This monomer is known in the art.

Synthesis of 1-(4-bromobutyldimethylsilyl)-1-propyne

This novel monomer was synthesized by adding 6.7 g (0.029 mole) of 4-bromobutyldimethylchlorosilane dropwise at 0° C. to a stirred solution of propynyllithium (1.34 g, 0.029 mole) in 50 ml of dry diethyl ether. The reaction mixture was stirred overnight at 25° C. and then poured into 400 ml of ice water. The ether layer was washed with distilled water, separated, and dried over MgSO$_4$. The ether layer was then filtered and the product separated by removing the ether using a rotovapor. The resulting oil was purified by vacuum distillation and had a b.p. of 70°–75° C. at 15 mm Hg pressure. Yield was 75% of theoretical. 'H NMR confirmed the structure.

Synthesis of 4-bromobutyldimethylchlorosilane

Hexachloroplatinic acid hexahydrate (0.02 g, 0.039 mmole) was dissolved in a minimum of 2-propanol. This solution was dissolved in 75 ml toluene under argon. 2-propanol and water were removed by azeotropically distilling 25 ml of the toluene. The resulting solution was stirred and 6.17 g (0.046 mole) of 4-bromo-1-butene was added at 40° C. 4.32 g (0.046 mole) of dimethylchlorosilane was slowly added and the solution was heated to 60° C. and allowed to react for four hours. The mixture was distilled to remove the toluene. Further vacuum distillation yielded 8.0 g of product with a b.p. of 92°–95° C. at 5 mm Hg pressure. 'H NMR confirmed the structure.

Synthesis of 4-bromo-1-butene

The 4-bromo-1-butene used in the above synthesis was made by slowly adding 20 g (0.11 mole) of hexamethylphosphoric triamide to a 190° C., stirred solution of 1,4-dibromobutane (90 g, 0.42 mole). The product was distilled into a dry-ice cooled receiver, washed with distilled water, and redistilled at 98° to 100° C./760 mm Hg pressure. The product was 99% pure and 'H NMR confirmed the structure. This product is also available through commercial sources.

Synthesis of Polymers

Polymerization of 1-trimethylsilyl-1-propyne 1.4 grams (0.0125 mole) of 1-(trimethylsilyl)-1-propyne was slowly added at 80° C. to a stirred solution of 0.0859 grams tantalum pentachloride in 10 mls of dry toluene. The reaction mixture was heated for 16 hours, dissolved in a minimum of toluene, and then poured into methanol. The precipitated polymer was redissolved in toluene and reprecipitated with methanol to further purify the product. Yield was 1.25 grams or 89% of theoretical. 'H NMR confirmed the structure to be poly(1-(trimethylsilyl)-1-propyne). GPC indicated M$_w$=330,000 and M$_n$=122,500 for the resulting poly(1-(trimethylsilyl)-1-propyne).

Copolymerization of 1-(trimethylsilyl)-1-propyne and 1-(4-bromobutyldimethylsilyl)-1-propyne A mixture of 0.57 g (5.12 mmole) of 1-(trimethylsilyl)-1-propyne and 0.30 g (1.28 mmole) of 1-(4-bromobutyldimethylsilyl)-1-propyne was slowly added to an 80° C., 10 ml dry toluene solution containing 0.086 g (0.24 mmole) tantalum pentachloride and 0.11 g (0.24 mmole) triphenylbismuth. The reaction mixture was maintained at 80° C. for 16 hours, then dissolved in further amounts of toluene and precipitated out of solution by the addition of methanol. The polymeric product was purified by dissolving it in toluene and reprecipitating with methanol. Yield was 0.71 g, or about 80% of theoretical. 'H NMR confirmed the structure of the 20 mole percent halo functional copolymer. GPC indicated M$_w$=220,000 and M$_n$=88,000.

The copolymer product can be represented by the general formula

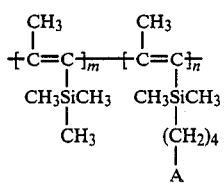

where A denotes a bromine atom.

Functionalization of the Copolymer of
1-trimethylsilyl-1-propyne and
1-(4-bromobutyldimethylsilyl)-1-propyne Methacrylate Functional Polymer 0.11 g of potassium methacrylate and a catalytic amount of tetrabutylammonium hydrogen sulfate (TBAH) was added to 20 mls of a tetrahydrofuran solution containing 0.2 g of poly(1-(trimethylsilyl)-1-propyne)-co-20 mole% poly(1-(4-bromobutyldimethylsilyl)-1-propyne) (CP). The reaction mixture was stirred overnight at 60° C. The polymer was then precipitated with methanol and purified by reprecipitation yielding 0.18 g of product. NMR indicated the structure to be represented by formula (IV) where A denotes a methacrylate radical.

Styrene Functional Polymer 0.1 g of 4-vinyl potassium benzoate and a catalytic amount of TBAH were added to 0.2 g of CP in 20 mls of tetrahydrofuran. This reaction mixture was heated to 60° C. and maintained at that temperature overnight. The polymer was precipitated and purified by reprecipitation with methanol yielding 0.19 g product. NMR confirmed the structure was represented by general formula (IV) where A denotes a radical with the general formula

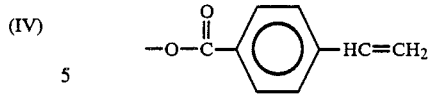

Quaternary Ammonium Salt Functional Polymers 1.0 g of triethylamine was added to 0.2 g of CP in 10 ml tetrahydrofuran and 10 ml dimethylformamide. The solution was heated to 60° C. overnight under argon and the resultant polymer was obtained by precipitation. The product was represented by formula (IV) when A denotes the radical —N$^+$(CH$_2$CH$_3$)$_3$Br—

Acetate Functional Polymer 0.1 g of potassium acetate and a catalytic amount of TBAH were added to 0.2 g of CP in 20 mls of tetrahydrofuran. The mixture was stirred overnight at 60° C. and the product was collected and purified by precipitation. The structure of the product was confirmed by NMR and was denoted by general structure (IV) where A denotes the radical

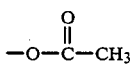

Alcohol Functional Polymer 0.05 g of TBAH and 2 mls of 50% NaOH in water were added to 0.2 g CP in 20 mls of tetrahydrofuran. The reaction mixture was left overnight at 60° C. The mixture was acidified to pH 5 and the polymer was precipitated. The structure of the polymer was determined by NMR to be consistent with formula (IV) where A denotes —OH.

What is claimed is:

1. A composition represented by the general formula

A(CH$_2$)$_x$SiR$_2$—C≡C—(CH$_2$)$_y$CH$_3$ where A denotes a halogen atom, R is an alkyl radical with 1 to 6 carbon atoms, x is an integer from 1 to 10, and y is an integer from 0 to 3.

2. The composition of claim 1 where A is a bromine atom, R denotes a methyl radical, x is 4 and y is 0.

* * * * *